United States Patent [19]

Conrad et al.

[11] 4,198,323
[45] Apr. 15, 1980

[54] 2,2,5-TRIMETHYL-5-PHENYL-1,3-DIOXANE AND PERFUME COMPOSITIONS CONTAINING IT

[75] Inventors: Jens Conrad, Hilden; Ulf-Armin Schaper, Dusseldorf; Klaus Bruns, Krefeld-Traar, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 923,794

[22] Filed: Jul. 12, 1978

[30] Foreign Application Priority Data

Jul. 29, 1977 [DE] Fed. Rep. of Germany ....... 2734295

[51] Int. Cl.$^2$ .......................... C11B 9/00; A61K 7/46
[52] U.S. Cl. ............................... 252/522 R; 260/340.7
[58] Field of Search ...................... 252/522; 260/340.7

[56] References Cited

U.S. PATENT DOCUMENTS

| | | | |
|---|---|---|---|
| 2,993,055 | 7/1961 | Hennis et al. | 260/340.9 |
| 3,239,421 | 3/1966 | Bengelsdorf | 252/522 R |
| 3,884,841 | 5/1975 | Maesseu et al. | 252/522 R |
| 4,113,664 | 9/1978 | Conrad | 252/522 R |

OTHER PUBLICATIONS

Chem. Ab. 66:37850r, 1967.

*Primary Examiner*—Veronica O'Keefe
*Attorney, Agent, or Firm*—Hammond & Littell, Weissenberger and Muserlian

[57] ABSTRACT

2,2,5-Trimethyl-5-phenyl-1,3-dioxane and a perfumery composition consisting essentially of from 1% to 50% by weight of 2,2,5-trimethyl-5-phenyl-1,3-dioxane and the remainder, customary constituents of perfumery compositions.

3 Claims, No Drawings

2,2,5-TRIMETHYL-5-PHENYL-1,3-DIOXANE AND PERFUME COMPOSITIONS CONTAINING IT

BACKGROUND OF THE INVENTION

Various 1,3-dioxanes and their use as perfumes are described in the following:

U.S. Pat. No. 3,884,841 — 2-n-Butyl-4,4,6-trimethyl-1,3-dioxane,

British Pat. No. 981,285 — 2,4-Dialkyl-1,3-dioxanes, 2,4,5-trialkyl-1,3-dioxanes and 2,4,5,6-tetraalkyl-1,3-dioxanes.

These compounds are alkylated 1,3-dioxanes. In addition, Rondestvedt, J. Org. Chem., Vol. 26, pp. 2247–2253 (1961), describes a number of 1,3-dioxanes without indication of any utility for the same, among which are 2-phenyl-5,5-dimethyl-1,3-dioxane, 2-(p-methylphenyl)-5,5-dimethyl-1,3-dioxane and 2-isopropyl-5,5-diphenyl-1,3-dioxane.

OBJECTS OF THE INVENTION

An object of the present invention is the development of perfumery compositions with characteristic fragrances and excellent adhesion.

Another object of the present invention is the development of a perfumery composition consisting essentially of from 1% to 50% by weight of 2,2,5-trimethyl-5-phenyl-1,3-dioxane having the formula

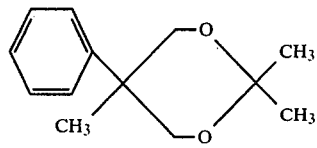

and the remainder, customary constituents of perfumery compositions.

A yet further object of the present invention is the obtaining of the aforesaid 2,2,5-trimethyl-5-phenyl-1,3-dioxane.

These and other objects of the invention will become more apparent as the description thereof proceeds.

DESCRIPTION OF THE INVENTION

It has been found that 2,2,5-trimethyl-5-phenyl-1,3-dioxane of the formula

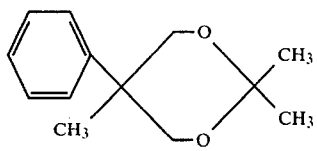

constitutes a valuable new perfume which can be used to advantage in a wide variety of perfume compositions.

The invention, therefore, relates also to a perfumery composition consisting essentially of from 1% to 50% by weight of 2,2,5-trimethyl-5-phenyl-1,3-dioxane having the formula

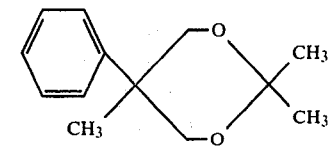

and the remainder, customary constituents of perfumery compositions.

The novel compound in accordance with the invention is produced by conventional methods of organic chemistry by transketalization of 2,2-dimethoxypropane with 2-methyl-2-phenyl-propanediol-(1,3) under acid catalysis at room temperature or slightly elevated temperature. A particularly successful catalyst has proved to be p-toluenesulfonic acid. The reaction occurs according to the following flow diagram:

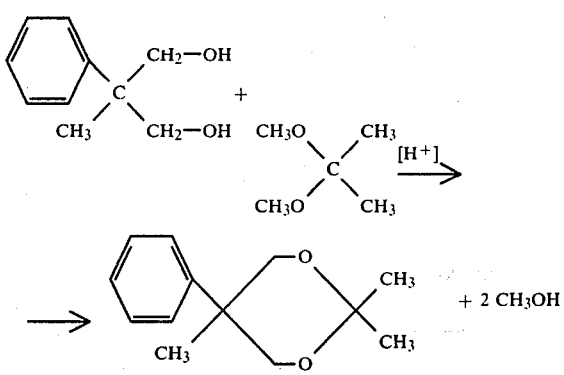

The perfume in accordance with the invention is distinguished by a particularly intensive and lasting, flowery, rosy-fruity fragrance of high quality and fullness. A further advantage of the novel perfume is that it can be combined very satisfactorily to form flowery perfume compositions and novel fragrances, and it also has a high degree of adherence.

The novel perfume in accordance with the invention can be mixed with other perfumes in a wide variety of quantity ratios to form flowery and novel perfume compositions. In general, however, the quantity of the novel perfume in the perfume composition will range between 1% to 50% by weight relative to the total composition. The remainder of the composition is conventional perfumery constituents. Compositions of this type can be used directly as a perfume or, alternatively, for perfuming cosmetics, such as creams, lotions, toilet waters, aerosols, mouthwashes, toilet soaps, etc.

The following examples are intended to explain further the subject of the invention, but without limiting the invention to these examples.

EXAMPLE 1

Production of 2,2,5-trimethyl-5-phenyl-1,3-dioxane 166 gm (1 mol) of 2-methyl-2-phenyl-propanediol-(1,3) were mixed with 114.5 gm (1.1 mol) of 2,2-dimethoxypropane and 2 gm of p-toluene-sulfonic acid. The mixture cooled off and the diol slowly dissolved. The reaction temperature was maintained at 20° to 25° C. by heating on a water bath. The mixture was homogeneous, and the reaction had terminated after approximately one hour. The product was fractionated in vacuo after distilling off the methanol formed and nonreacted 2,2-dimethoxypropane at normal pressure. 175 gm of 2,2,5-trimethyl-5-phenyl-1,3-dioxane having a boiling point of 135° C./13 Torr and refractive index of $n_D^{20}$ 1.5124, were obtained, corresponding to a yield of 85% of theory. The compound is distinguished by a fresh, flowery, long-adhering, somewhat rosy-fruity fragrance.

EXAMPLE 2

Production of a Rose Composition

|  | Parts by Weight |
| --- | --- |
| 2,2,5-trimethyl-5-phenyl-1,3-dioxane | 140 |
| Phenylethyl alcohol | 160 |
| Hydroxy citronellal | 160 |
| Methylethylacetic acid phenyl ethyl ester | 120 |
| Citronella oil, extra | 100 |
| Geranium oil, extra | 80 |
| Guaiyl acetate | 80 |
| Geranyl acetate | 40 |
| Dimethylbenzyl carbinyl acetate | 40 |
| α-Ionone | 40 |
| Nerol | 40 |
|  | 1,000 |

EXAMPLE 3

Production of a Lily of the Valley Composition

|  | Parts by Weight |
| --- | --- |
| 2,2,5-trimethyl-5-phenyl-1,3-dioxane | 160 |
| Lyral | 280 |
| Linalool | 100 |
| Dimethylbenzyl carbinol | 100 |
| Geranium oil ex palmrosa | 100 |
| Jasmonis (Givaudan) | 50 |
| Cinnamyl alcohol | 40 |

-continued

|  | Parts by Weight |
| --- | --- |
| Nerol | 40 |
| Guaiyl acetate | 30 |
| α-Ionone | 30 |
| Ylang abs. | 20 |
| Dimethylbenzyl carbinyl acetate | 20 |
| Terpinol | 10 |
| Heliotropine | 10 |
| Cyclamen aldehyde | 5 |
| Lauryl alcohol | 2 |
| Ethyl vanillin | 1 |
| cis-Hexenol (10% solution) | 1 |
| Methylheptenone (10% solution) | 1 |
|  | 1,000 |

The preceding specific embodiments are illustrative of the practice set of the invention. It is to be understood, however, that other expedients known to those skilled in the art or disclosed herein, may be employed without departing from the spirit of the invention or the scope of the appended claims.

We claim:

1. 2,2,5-Trimethyl-5-phenyl-1,3-dioxane.

2. A perfumery composition consisting essentially of from 1% to 50% by weight of 2,2,5-trimethyl-5-phenyl-1,3-dioxane having the formula:

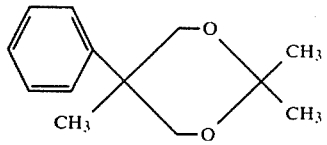

and the remainder, customary constituents of perfumery compositions.

3. The perfumery composition of claim 2 wherein said customary constituents of perfumery compositions include at least one other perfume.

* * * * *